(12) United States Patent
Bobba et al.

(10) Patent No.: US 11,377,445 B2
(45) Date of Patent: Jul. 5, 2022

(54) DERIVATIVES OF PALIPERIDONE AND PROCESS FOR THE PREPARATION THEREOF

(71) Applicant: Zenvision Pharma LLP, Mumbai (IN)

(72) Inventors: Sivakumar Venkata Bobba, Navi Mumbai (IN); Eswar Rao Kodali, Navi Mumbai (IN)

(73) Assignee: Zenvision Pharma LLP, Mumbai (IN)

( * ) Notice: Subject to any disclaimer, the term of this patent is extended or adjusted under 35 U.S.C. 154(b) by 0 days.

(21) Appl. No.: 16/962,718

(22) PCT Filed: Nov. 23, 2018

(86) PCT No.: PCT/IB2018/059245
§ 371 (c)(1),
(2) Date: Jul. 16, 2020

(87) PCT Pub. No.: WO2019/162746
PCT Pub. Date: Aug. 29, 2019

(65) Prior Publication Data
US 2020/0354360 A1 Nov. 12, 2020

(30) Foreign Application Priority Data
Feb. 21, 2018 (IN) .............................. 201821006549

(51) Int. Cl.
*C07D 471/04* (2006.01)
(52) U.S. Cl.
CPC .................. *C07D 471/04* (2013.01)
(58) Field of Classification Search
None
See application file for complete search history.

(56) References Cited

FOREIGN PATENT DOCUMENTS

EP 0368388 A2 5/1990

OTHER PUBLICATIONS

PCT Search Report dated Feb. 21, 2019, Application No. PCT/IB2018/059245.
PCT Written Opinion dated Feb. 21, 2019, Application No. PCT/IB2018/059245.

*Primary Examiner* — Nannette Holloman
(74) *Attorney, Agent, or Firm* — The Dobrusin Law Firm, PC

(57) ABSTRACT

The present disclosure relates to novel hydroxyl or halogen substituted derivatives of $C_{11}$-$C_{22}$ alkanoic acid ester of Paliperidone compound of formula (formula II) and process for preparing the same. The said compounds used in pharmaceutical composition for the treatment of schizophrenia and schizoaffective disorder, wherein, R=$C_{10}$-$C_{21}$ alkyl substituted by hydroxy or halogen.

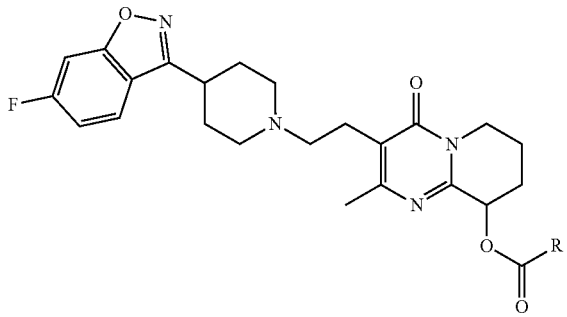

11 Claims, 2 Drawing Sheets

DERIVATIVES OF PALIPERIDONE AND PROCESS FOR THE PREPARATION THEREOF

FIELD OF THE INVENTION

Figure 1:
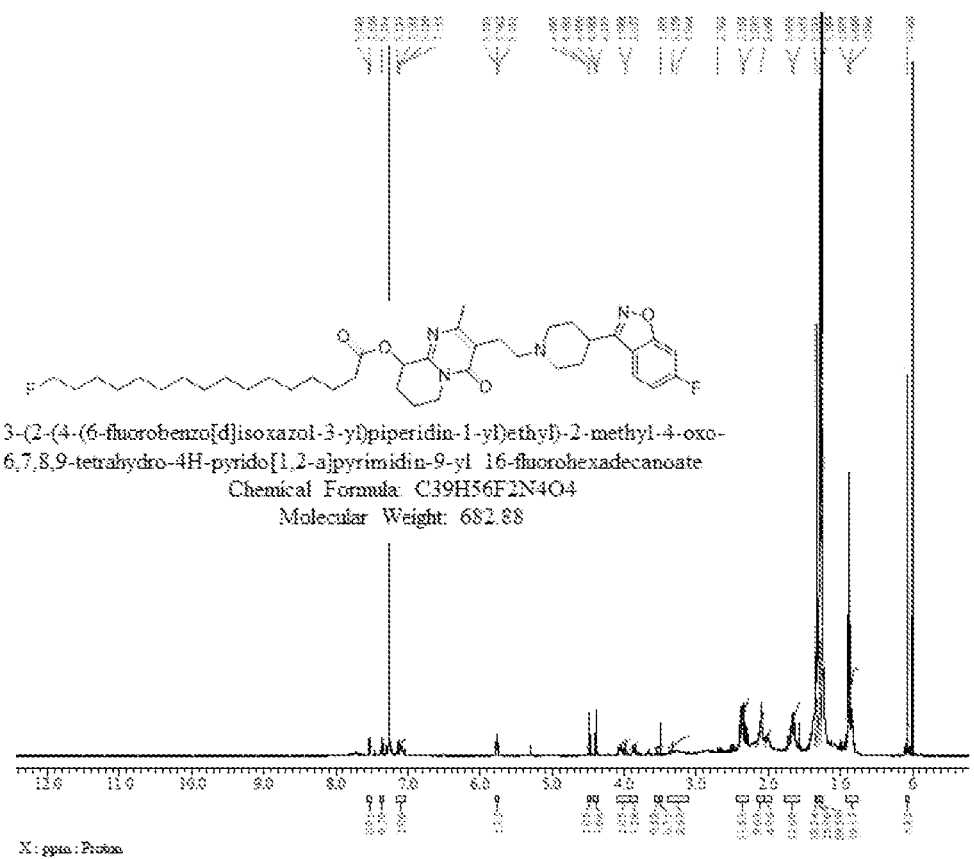

The present invention relates to novel derivatives of Paliperidone and process for the preparation thereof.

BACKGROUND OF THE INVENTION

Paliperidone is a psychotropic agent belonging to the chemical class of benzisoxazole derivatives. Also it is the primary active metabolite of the older antipsychotic risperidone. The chemical name is (±)-3-[2-[4-(6-fluoro-1, 2-benzisoxazol-3-yl)-1-piperidinyl]ethyl]-6, 7, 8, 9-tetrahydro-9-hydroxy-2-methyl-4Hpyrido[1,2-a]pyrimidin-4-one. Its molecular formula is $C_{23}H_{27}FN_4O_3$ and its molecular weight is 426.49. Paliperidone is represented by compound of structural formula I

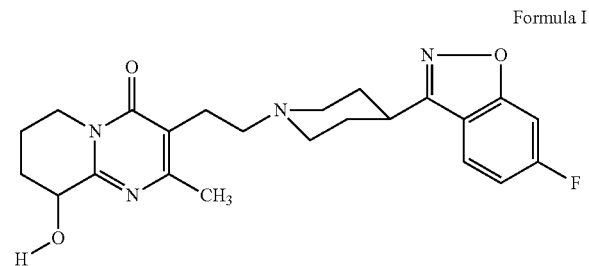 [SMILES: Cc1nc2n(c(=O)c1CCN1CCC(c3noc4cc(F)ccc34)CC1)CCCC2O]

Formula I

Paliperidone is sparingly soluble in 0.1N HCl and methylene chloride; practically insoluble in water, 0.1N NaOH, and hexane; and slightly soluble in N, N-dimethylformamide.

Paliperidone palmitate is very slightly soluble in ethanol and methanol, practically insoluble in polyethylene glycol 400 and propylene glycol, and slightly soluble in ethyl acetate.

The Paliperidone extended release tablet of Janssen Pharmaceuticals Inc has been approved in USA as on Dec. 19, 2006 under the trade name INVEGA® and is available in the strength 1.5 mg (orange-brown), 3 mg (white), 6 mg (beige), and 9 mg (pink). INVEGA® utilizes OROS® osmotic drug release technology. The product is indicated for the treatment of schizophrenia and schizoaffective disorder as monotherapy and an adjunct to mood stabilizers and/or antidepressant therapy.

The Paliperidone palmitate sterile aqueous extended-release suspension for intramuscular injection of Janssen Pharmaceuticals Inc has been approved in USA as on Jul. 31, 2009 under the trade name INVEGA SUSTENNA® and is available in the strength 39 mg (0.25 mL), 78 mg (0.5 mL), 117 mg (0.75 mL), 156 mg (1.0 mL), and 234 mg (1.5 mL). The product is indicated for the treatment of schizophrenia in adults and schizoaffective disorder in adults as monotherapy and an adjunct to mood stabilizers and/or antidepressant therapy.

The Paliperidone Palmitate sterile aqueous extended-release suspension for intramuscular 3-month injection of Janssen Pharmaceuticals Inc has been approved in USA as on May 18, 2015 under the trade name INVEGA TRINZA® and is available in the strength 273 mg, 410 mg, 546 mg, and 819 mg Paliperidone palmitate. The product is indicated for the treatment of schizophrenia in patients after they have been adequately treated with INVEGA SUSTENNA® (1-month Paliperidone palmitate extended-release injectable suspension) for at least four months.

U.S. Pat. No. 6,077,843 generically discloses pharmaceutical composition suitable as a depot formulation for administration via intramuscular or subcutaneous injection, comprising Paliperidone esters or a salt and a pharmaceutically acceptable carrier. This patent reference also generically discloses derivatives of Paliperidone like decanoic (capric), undecanoic, dodecanoic (lauric), tridecanoic, tetradecanoic (myristic), pentadecanoic, hexadecanoic (palmitic), heptadecanoic, octadecanoic (stearic), nonadecanoic and eicosanoic acid. However, this patent does not disclose or teaches novel hydroxyl and halogen substituted derivatives of $C_{11}$-$C_{22}$ alkanoic acid ester of Paliperidone and process of preparing the same.

U.S. Pat. No. 9,439,906 discloses a dosing regimen for intramuscular administering Paliperidone palmitate sustained release formulation to a psychiatric patient in need of treatment for schizophrenia, schizoaffective disorder, or schizophreniform disorder.

U.S. Patent Publication No. 20120100188 discloses solid state form of salt of Paliperidone is an L-(+)-tartrate salt, a tosylate salt, a maleate salt, an oxalate salt, an acetate salt or a malate salt.

PCT Publication No. WO2009060297 discloses certain acid addition salts of paliperidone derived from an acid selected from hydrochloric acid, hydrobromic acid, hydroiodic acid, ortho phosphoric acid, fumaric acid or oxalic acid. The WO'297 publication further discloses crystalline forms of paliperidone hydrochloride, paliperidone hydrobromide, paliperidone phosphate and paliperidone fumarate, and characterizes them by powder X-ray diffraction.

Currently, the commercially marketed product of Paliperidone is available in the form of tablet, extended release tablet and long acting injection. The commercially available extended release tablet and Injection contains Paliperidone and Paliperidone Palmitate respectively.

The physicochemical properties of available salts and derivatives for Paliperidone known in the prior art impacts stability and efficacy of the product in the treatment of schizophrenia and schizoaffective disorder.

Therefore, there is need in art to develop novel derivatives of Paliperidone i.e. hydroxyl and halogen substituted derivatives of $C_{11}$-$C_{22}$ alkanoic acid ester of Paliperidone and process of preparing the same.

Accordingly, the present invention provides novel derivatives of Paliperidone i.e. hydroxyl and halogen substituted derivatives of $C_{11}$-$C_{22}$ alkanoic acid ester of Paliperidone and process of preparing the same.

The novel derivatives of the present invention have superior physicochemical properties provide better patient compliance and efficacy in the treatment of schizophrenia and schizoaffective disorder.

OBJECTS OF THE INVENTION

Accordingly, it is an object of the present invention to provide novel hydroxyl substituted derivatives of $C_{11}$-$C_{22}$ alkanoic acid ester of Paliperidone.

It is another object of the present invention to provide novel hydroxyl substituted derivatives of $C_{11}$-$C_{22}$ alkanoic acid ester of Paliperidone; preferably 16-hydroxypalmitate of Paliperidone.

It is another object of the present invention to provide novel halogen substituted derivatives of $C_{11}$-$C_{22}$ alkanoic acid ester of Paliperidone.

It is another object of the present invention to provide novel halogen substituted derivatives of $C_{11}$-$C_{22}$ alkanoic acid ester of Paliperidone; preferably 16-fluoropalmitate of Paliperidone or 16-bromopalmitate of Paliperidone.

It is another object of the present invention to provide novel and commercially viable process with ease of operations for the preparation of hydroxyl substituted derivatives of $C_{11}$-$C_{22}$ alkanoic acid ester of Paliperidone by use of one or more intermediate; preferably process of preparation of 16-hydroxypalmitate of Paliperidone.

It is another object of the present invention to provide novel and commercially viable process with ease of operations for the preparation of halogen substituted derivatives of $C_{11}$-$C_{22}$ alkanoic acid ester of Paliperidone by use of one or more intermediate; preferably process of preparation of 16-fluoropalmitate of Paliperidone or 16-bromopalmitate of Paliperidone.

It is another object of the present invention to provide method of treating schizophrenia and schizoaffective disorder by administrating the composition comprising novel hydroxyl or halogen substituted derivatives of $C_{11}$-$C_{22}$ alkanoic acid ester of Paliperidone.

It is another object of the present invention to provide method of treating schizophrenia and schizoaffective disorder by administrating the composition comprising 16-hydroxypalmitate of Paliperidone 16-fluoropalmitate of Paliperidone or 16-bromopalmitate of Paliperidone.

SUMMARY OF THE INVENTION

A first aspect of the present invention is to provide novel hydroxyl and halogen substituted derivatives of $C_{11}$-$C_{22}$ alkanoic acid ester of Paliperidone compound of formula-II.

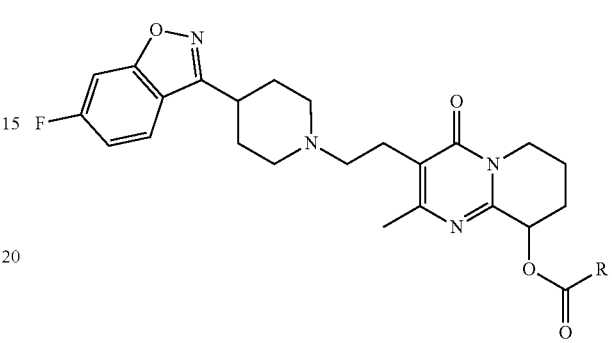

Formula-II

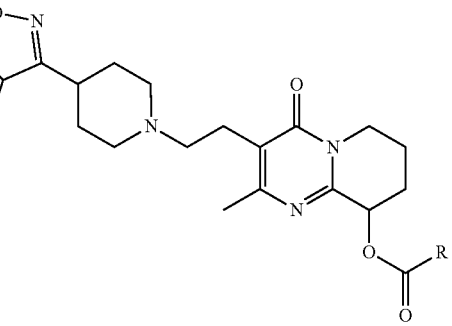

Wherein R = $C_{10}$-$C_{21}$ straight and brached alkylsubstituted by hydroxy or halogen
Substituted derivatives of $C_{11}$-$C_{22}$ alkanoic acid ester of Paliperidone In another aspect of the present invention provides a novel hydroxypalmitate and halopalmitate derivatives of Paliperidone.

In another aspect of the present invention provides a novel 16-hydroxypalmitate, 16-fluoropalmitate and 16-bromopalmitate derivatives of Paliperidone.

In another aspect of the present invention provides a process for preparation of novel hydroxyl and halogen substituted derivatives of $C_{11}$-$C_{22}$ alkanoic acid ester of Paliperidone.

In another aspect of the present invention provides a process for preparation of novel hydroxyl and halogen substituted derivatives of $C_{11}$-$C_{22}$ alkanoic acid ester of Paliperidone by use of one or more intermediate.

In another aspect of the present invention provides a process for preparation of novel hydroxyl and halogen substituted derivatives of $C_{11}$-$C_{22}$ alkanoic acid ester of Paliperidone compound of formula-II comprises the step of reacting Paliperidone with halogen or hydroxyl substituted alkanoyl chloride as represented by Scheme-I Scheme-I

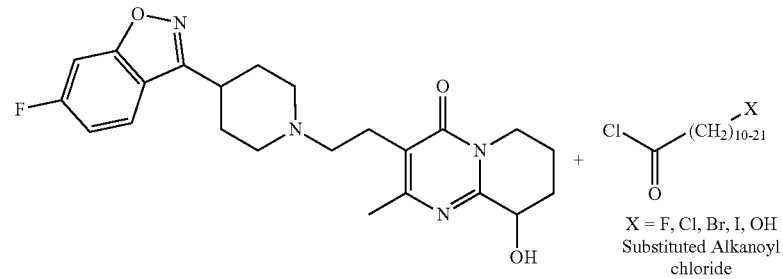

3-[2-[4-(6-Fluoro-1,2-benzisoxazol-3-yl)-1-piperidinyl]
ethyl]-6,7,8,9-tetrahydro-9-hydroxy-2-methyl-4H-
pyrido[1,2-a]pyrimidin-4-one X = F, Cl, Br, I, OH
Substituted Alkanoyl chloride

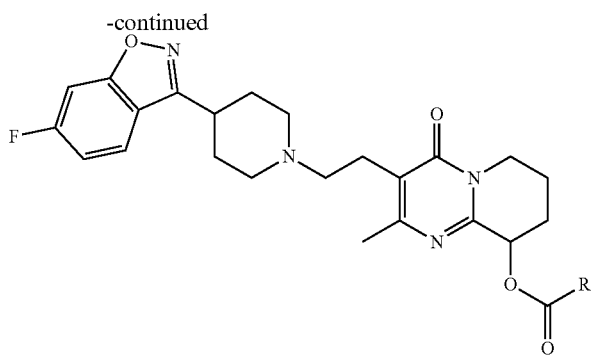

Wherein R = $C_{10}$-$C_{21}$ straight and brached
alkylsubstituted by hydroxy or halogen
Substituted derivatives of $C_{11}$-$C_{22}$ alkanoic
acid ester of Paliperidone
Formula-II In another aspect of the present invention provides a process for preparation of novel hydroxyl and halogen substituted derivatives of $C_{11}$-$C_{22}$ alkanoic acid ester of Paliperidone which comprises the step of reacting Paliperidone with halogen or hydroxy substituted alkanoyl chloride in the presence of one or more solvents or reagents.

In another aspect of the present invention provides a process for preparation of novel hydroxyl and halogen substituted derivatives of $C_{11}$-$C_{22}$ alkanoic acid ester of Paliperidone compound of formula-II, comprises the step of reacting Paliperidone with halogen or hydroxy substituted anhydride and mixed anhydride.

In another aspect of the present invention provides a process for preparation of novel 16-hydroxypalmitate, 16-fluoropalmitate and 16-bromopalmitate derivative of Paliperidone.

In another aspect of the present invention provides a process of preparing novel 16-hydroxypalmitate, 16-fluoropalmitate and 16-bromopalmitate of Paliperidone by use of one or more intermediate.

In another aspect of the present invention provides a process of preparing novel 16-hydroxypalmitate derivatives of Paliperidone compound of Formula-III comprises the step of reacting Paliperidone with 16-Hydroxyhexadecanoyl chloride.

In another aspect of the present invention provides a process of preparing novel 16-hydroxypalmitate derivatives of Paliperidone comprises the step of reacting Paliperidone with 16-Hydroxyhexadecanoyl chloride in the presence of one or more solvent or reagents.

In another aspect of the present invention provides a process of preparing novel 16-fluoropalmitate or 16-bromopalmitate derivatives of Paliperidone compound of formula-IV comprises the step of reacting Paliperidone with 16-fluorohexadecanoyl chloride or 16-bromohexadecanoyl chloride respectively.

In another aspect of the present invention provides a process of preparing novel 16-fluoropalmitate or 16-bromopalmitate derivatives of Paliperidone comprises the step of reacting Paliperidone with 16-fluorohexadecanoyl chloride or 16-bromohexadecanoyl chloride respectively in the presence of one or more solvent or reagents.

In another aspect of the present invention is to provide pharmaceutical composition comprising novel hydroxyl and halogen substituted derivatives of $C_{11}$-$C_{22}$ alkanoic acid ester of Paliperidone along with one or more pharmaceutically acceptable excipient.

In another aspect of the present invention is to provide pharmaceutical composition comprising novel 16-hydroxypalmitate or 16-fluoropalmitate or 16-bromopalmitate derivatives of Paliperidone along with one or more pharmaceutically acceptable excipient.

In another aspect of the present invention is to provide pharmaceutical composition comprising novel hydroxyl and halogen substituted derivatives of $C_{11}$-$C_{22}$ alkanoic acid ester of Paliperidone for the treatment of schizophrenia and schizoaffective disorder.

In another aspect of the present invention provides a pharmaceutical composition comprising novel 16-hydroxypalmitate or 16-fluoropalmitate or 16-bromopalmitate of Paliperidone for the treatment of schizophrenia and schizoaffective disorder.

BRIEF DESCRIPTION OF ACCOMPANYING FIGURES

FIG. 1: Illustrates the $^1$H NMR Spectrum of 16-fluoropalmitate of Paliperidone.

Figure 2:
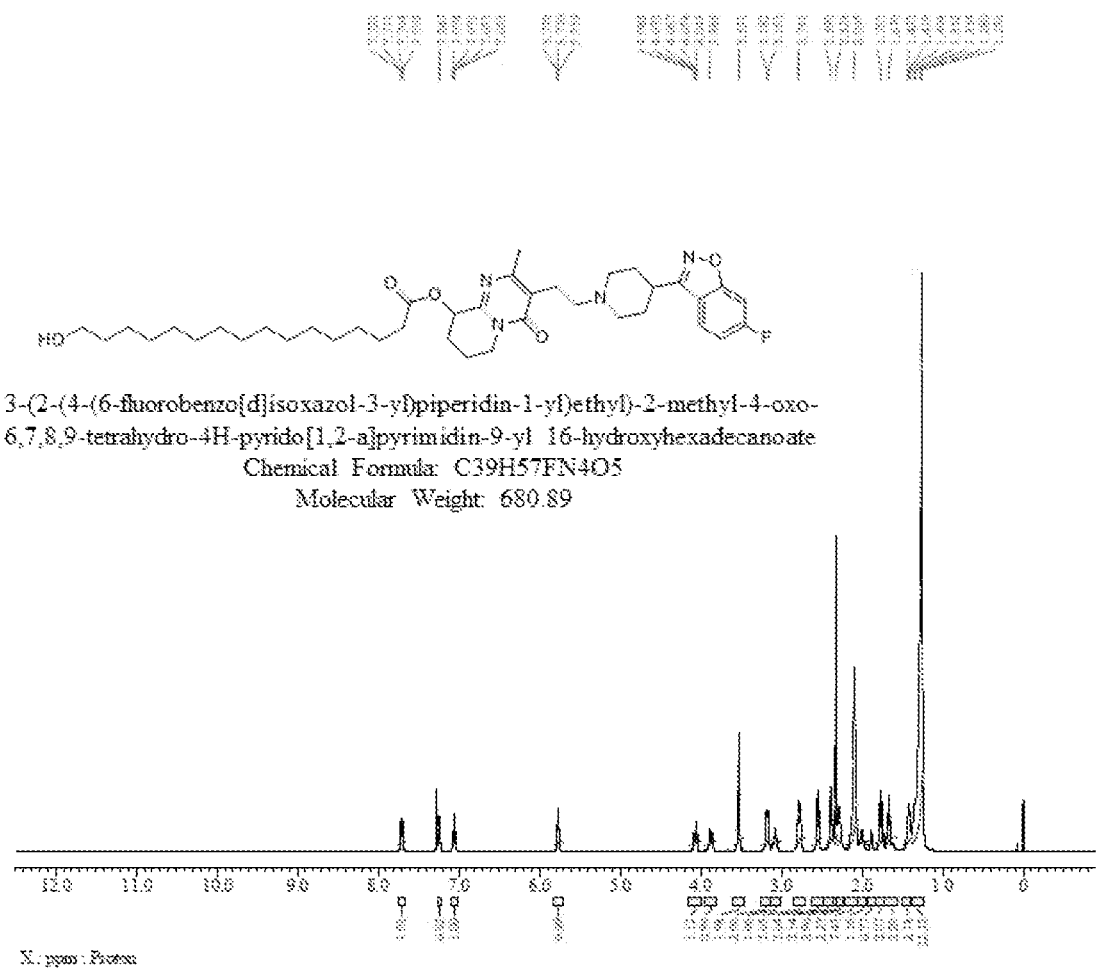

FIG. 2: Illustrates the $^1$H NMR Spectrum of 16-hydroxypalmitate of Paliperidone.

DETAIL DESCRIPTION OF THE INVENTION

The present invention provides novel derivatives of Paliperidone and process of preparation thereof.

The novel derivatives of Paliperidone according to present invention are hydroxyl or halogen substituted derivatives of $C_{11}$-$C_{22}$ alkanoic acid ester of Paliperidone of Formula-II.

Formula-II

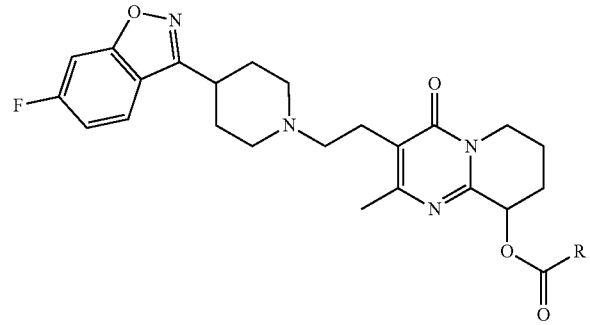

Wherein R = $C_{10}$-$C_{21}$ straight and brached
alkylsubstituted by hydroxy or halogen
Substituted derivatives of $C_{11}$-$C_{22}$ alkanoic acid ester
of Paliperidone The halogen atoms according to present invention may be the F, Cl, Br or I.

The novel hydroxyl or halogen substituted derivatives of $C_{11}$-$C_{22}$ alkanoic acid ester of Paliperidone compound of Formula-II; wherein hydroxyl or halogen group can be substituted at any position of carbon of alkanoic acid.

The novel hydroxyl or halogen substituted derivatives of $C_{11}$-$C_{22}$ alkanoic acid ester of Paliperidone compound of Formula-II; wherein alkanoic acid is the $C_{16}$ i.e. palmitic acid.

The novel hydroxyl or halogen substituted derivatives of palmitic acid ester of Paliperidone; wherein hydroxyl or halogen group can be substituted at any position of carbon of palmitic acid.

The novel hydroxyl or halogen substituted derivatives of palmitic acid ester of Paliperidone; wherein hydroxyl or halogen group is preferably substituted at $C_{16}$ of palmitic acid. Therefore, according to present invention said compound can be termed as 16-hydroxypalmitate of Paliperidone of Formula-III and 16-halopalmitate of Paliperidone; preferably 16-fluoropalmitate of Paliperidone of. Formula-IV or 16-bromopalmitate of Paliperidone of Formula-V.

Formula-III

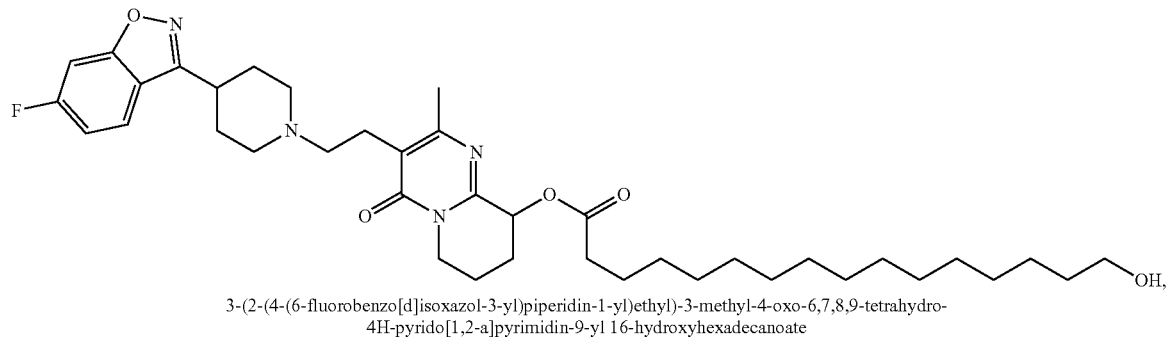

3-(2-(4-(6-fluorobenzo[d]isoxazol-3-yl)piperidin-1-yl)ethyl)-3-methyl-4-oxo-6,7,8,9-tetrahydro-4H-pyrido[1,2-a]pyrimidin-9-yl 16-hydroxyhexadecanoate Formula-IV

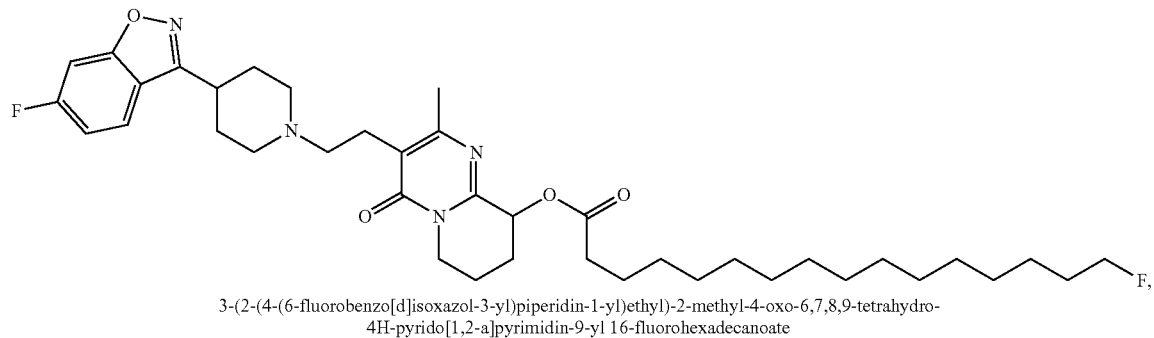

3-(2-(4-(6-fluorobenzo[d]isoxazol-3-yl)piperidin-1-yl)ethyl)-2-methyl-4-oxo-6,7,8,9-tetrahydro-4H-pyrido[1,2-a]pyrimidin-9-yl 16-fluorohexadecanoate Formula-V

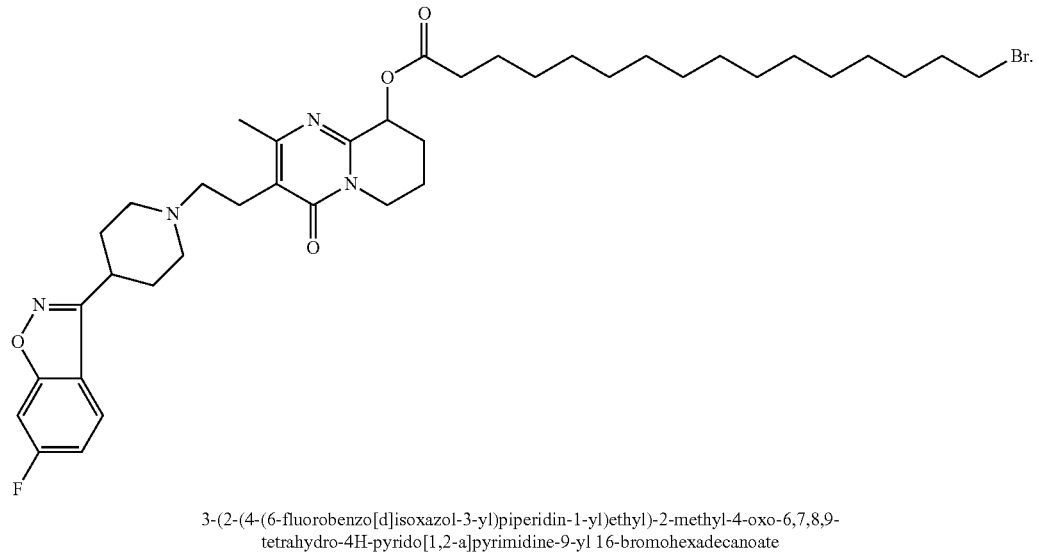

3-(2-(4-(6-fluorobenzo[d]isoxazol-3-yl)piperidin-1-yl)ethyl)-2-methyl-4-oxo-6,7,8,9-tetrahydro-4H-pyrido[1,2-a]pyrimidine-9-yl 16-bromohexadecanoate In another aspect of the present invention is to provide novel process for preparation of hydroxyl or halogen substituted derivatives of $C_{11}$-$C_{22}$ alkanoic acid ester of Paliperidone of Formula-II.

In another aspect of the present invention is to provide novel process for preparation of hydroxyl or halogen substituted derivatives of $C_{11}$-$C_{22}$ alkanoic acid ester of Paliperidone of Formula-II; wherein $C_{11}$-$C_{22}$ alkanoic acid is preferably $C_{16}$ i.e. palmitic acid.

The process of preparation of novel compounds according to present invention involves use of one or more solvents and reagents.

The one or more solvents according to present invention may be selected from but not limited to dichloromethane, methanol, acetone, ethanol, methyl ethyl ketone, methyl isobutyl ketone, dibutyl ketone, diethyl ketone, dipropyl ketone, diisopropyl ketone, methyl butyl ketone, methyl propyl ketone, methyl isopropyl ketone, ethyl isopropyl ketone, propanol, isopropanol, butanol, isobutanol, t-butanol, pentanol, dichloroethane, chloroform, carbon tetrachloride, tetrahydrofuran, dioxane, diethyl ether, diisopropyl ether, dibutyl ether, methyl tertiary butyl ether, methyl ethyl ether, methyl isobutyl ether, ethyl acetate, propyl acetate, isopropyl acetate, butyl acetate, tertiary butyl acetate, pentyl acetate, acetonitrile or propionitrile.

The one or more reagents according to present invention may be selected from but not limited to potassium carbonate, 4-dimethylaminopyridine, sodium carbonate, sodium sulphate, potassium sulphate, potassium carbonate, sodium hydroxide, potassium hydroxide, sodium bicarbonate, potassium bicarbonate, lithium hydroxide, lithium carbonate, triethylamine, diisopropylamine or pyridine.

The novel process for preparation of hydroxyl substituted derivatives of palmitic acid ester of Paliperidone; preferably 16-hydroxypalmitate of Paliperidone of Formula-III involves use of one or more intermediates.

The one or more intermediates for the preparation of 16-hydroxypalmitate of Paliperidone may include but not limited to hydroxyl substituted hexadecanoyl chloride or hydroxyl substituted anhydride or mixed anhydride or other. Preferably it is 16-hydroxyhexadecanoylchloride.

The process of preparation 16-hydroxypalmitate of Paliperidone according to present invention involves step of reacting Paliperidone of Formula-I with 16-hydroxyhexadecanoyl chloride in presence of dichloromethane and Potassium carbonate and 4-dimethylaminopyridine, which results in the formation of 16-hydroxypalmitate of Paliperidone of Formula-III which is represented by Scheme-II.

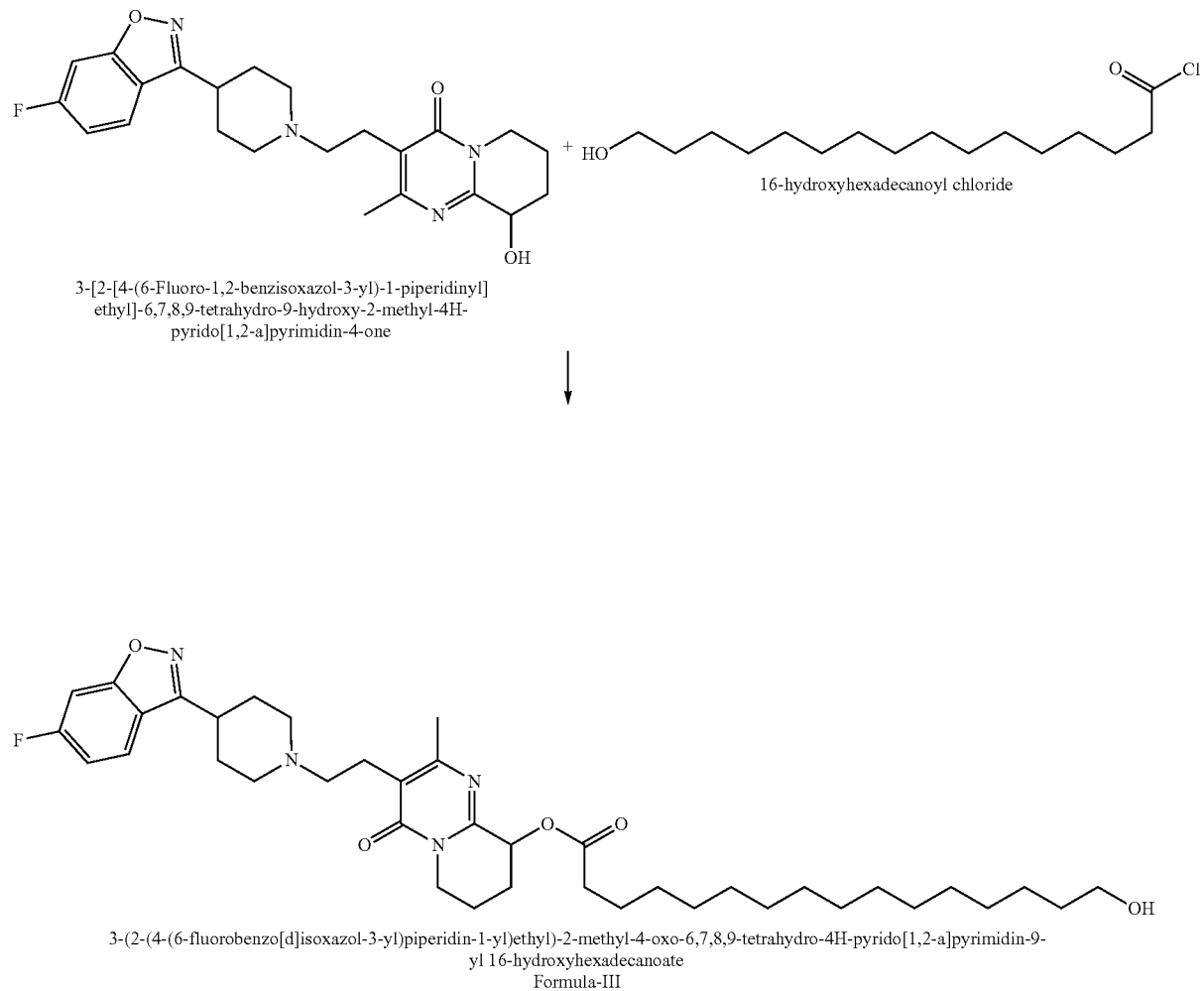

Scheme-II

3-[2-[4-(6-Fluoro-1,2-benzisoxazol-3-yl)-1-piperidinyl]
ethyl]-6,7,8,9-tetrahydro-9-hydroxy-2-methyl-4H-
pyrido[1,2-a]pyrimidin-4-one 16-hydroxyhexadecanoyl chloride 3-(2-(4-(6-fluorobenzo[d]isoxazol-3-yl)piperidin-1-yl)ethyl)-2-methyl-4-oxo-6,7,8,9-tetrahydro-4H-pyrido[1,2-a]pyrimidin-9-
yl 16-hydroxyhexadecanoate
Formula-III The intermediate used in the preparation of 16-hydroxypalmitate of Paliperidone i.e. 16-hydroxyhexadecanoyl chloride can be used directly or can be prepared from 16-hydroxyhexadecanoic acid as shown below.

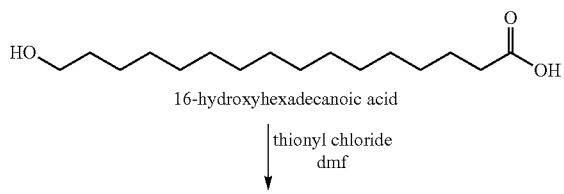

16-hydroxyhexadecanoic acid thionyl chloride
dmf

The novel process for preparation of 16-halopalmitate of Paliperidone, preferably 16-fluoropalmitate of Paliperidone of Formula-IV or 16-bromopalmitate of Paliperidone of Formula-V involves use of one or more intermediates.

The one or more intermediates for the preparation of 16-halopalmitate of Paliperidone may include but not limited to halogen substituted hexadecanoyl chloride or halogen substituted anhydride or mixed anhydride or other.

The process for the preparation of 16-fluoropalmitate of Paliperidone according to the present invention involves reacting Paliperidone of Formula-I with 16-flurohexadecanoyl chloride in presence of dichloromethane and Potassium carbonate and 4-dimethylaminopyridine, which results in the formation of 16-fluoropalmitate of Paliperidone of Formula-IV represented by Scheme-III.

Scheme-III

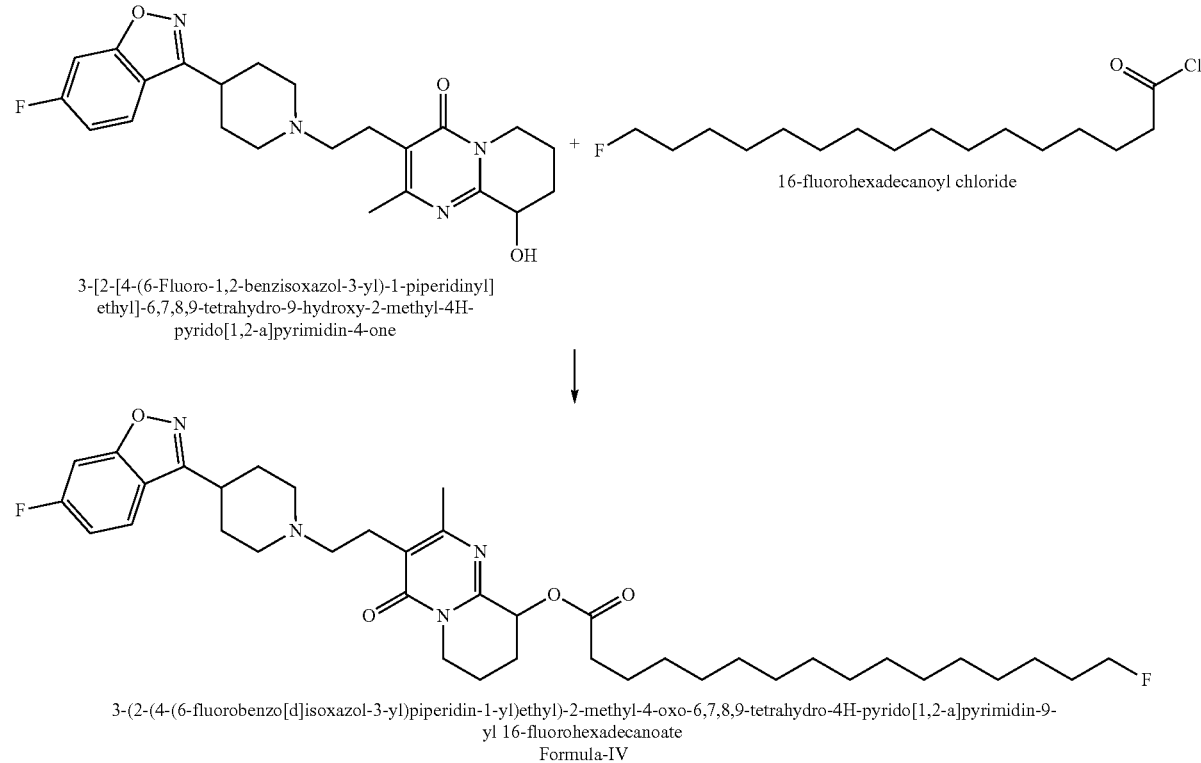

3-[2-[4-(6-Fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one 3-(2-(4-(6-fluorobenzo[d]isoxazol-3-yl)piperidin-1-yl)ethyl)-2-methyl-4-oxo-6,7,8,9-tetrahydro-4H-pyrido[1,2-a]pyrimidin-9-yl 16-fluorohexadecanoate
Formula-IV -continued

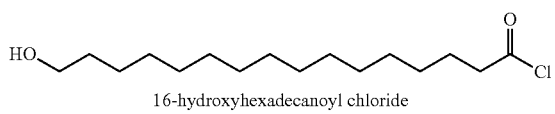

16-hydroxyhexadecanoyl chloride

In another aspect of the present invention is to provide novel process for preparation of halogen substituted derivatives of $C_{11}$-$C_{22}$ alkanoic acid ester of Paliperidone of Formula-II.

In another aspect of the present invention is to provide the process for preparation of halogen substituted derivatives of palmitic acid ester of Paliperidone i.e. 16-halopalmitate of Paliperidone; wherein halogen may be F, Cl, Br or I.

The intermediate used in the preparation of 16-fluoropalmitate of Paliperidone i.e. 16-fluorohexadecanoyl chloride can be used directly or can be prepared from one or more intermediates like methyl 16-hydroxyhexadecanoate or 16-hydroxyhexadecanoic acid as shown below.

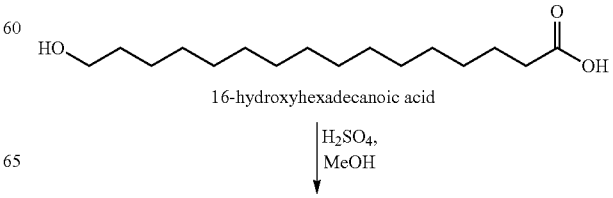

16-hydroxyhexadecanoic acid $H_2SO_4$,
MeOH

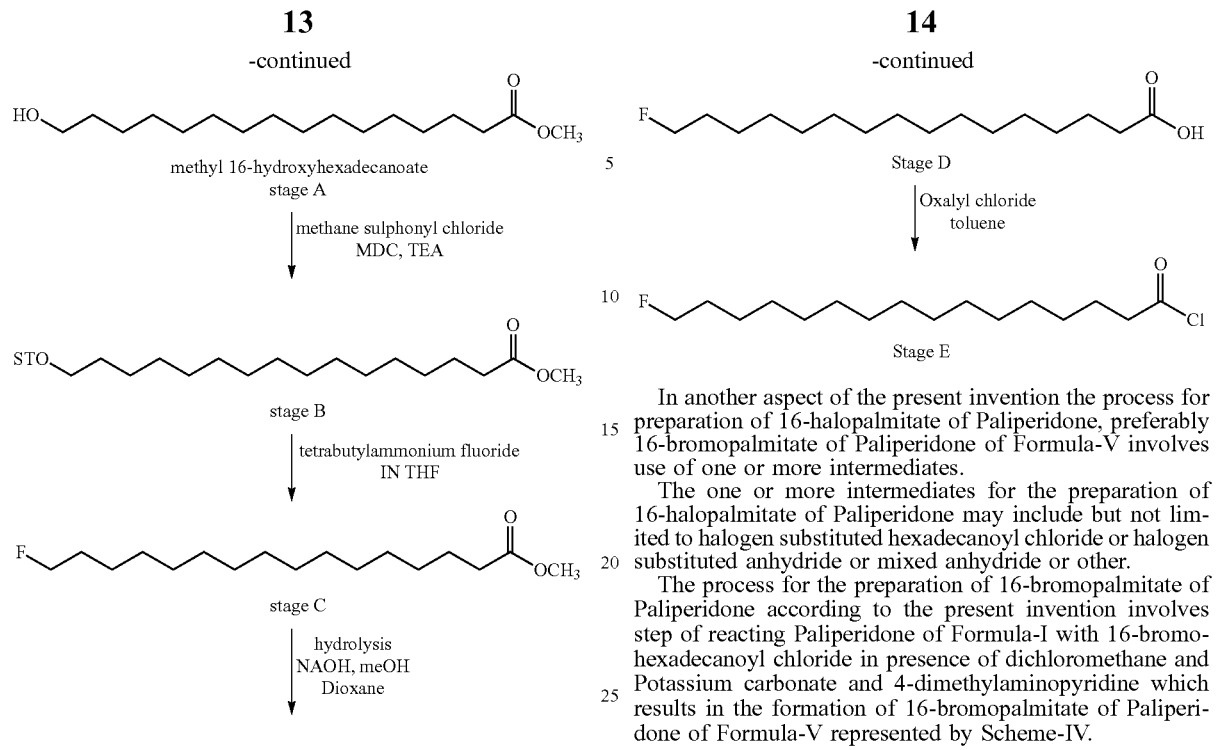

In another aspect of the present invention the process for preparation of 16-halopalmitate of Paliperidone, preferably 16-bromopalmitate of Paliperidone of Formula-V involves use of one or more intermediates.

The one or more intermediates for the preparation of 16-halopalmitate of Paliperidone may include but not limited to halogen substituted hexadecanoyl chloride or halogen substituted anhydride or mixed anhydride or other.

The process for the preparation of 16-bromopalmitate of Paliperidone according to the present invention involves step of reacting Paliperidone of Formula-I with 16-bromohexadecanoyl chloride in presence of dichloromethane and Potassium carbonate and 4-dimethylaminopyridine which results in the formation of 16-bromopalmitate of Paliperidone of Formula-V represented by Scheme-IV.

Scheme-IV

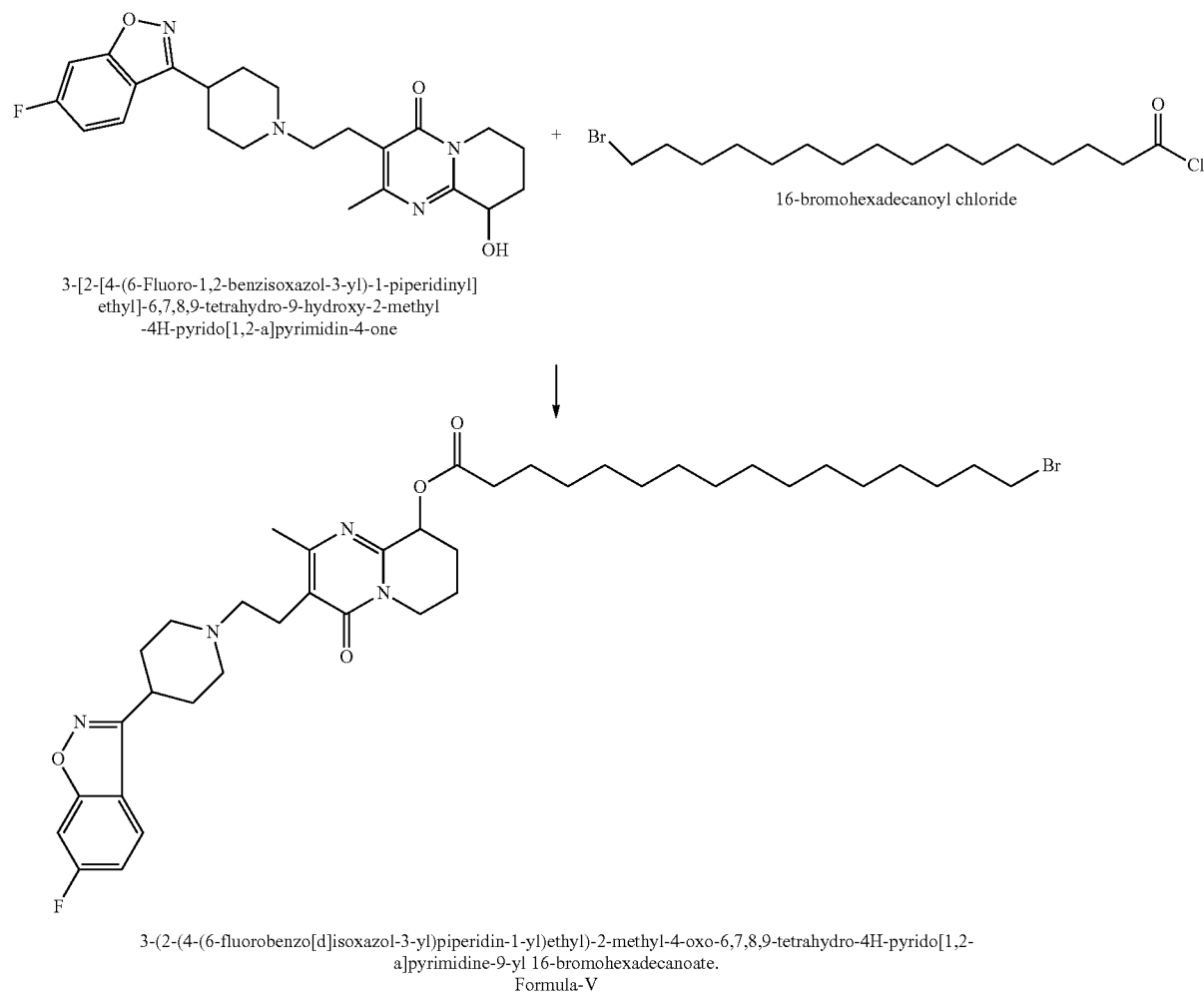

The intermediate used in the preparation of 16-bromopalmitate of Paliperidone i.e. 16-bromohexadecanoyl chloride can be used directly or can be prepared from one or more intermediates like 16-bromohexadecanoic acid or 16-hydroxyhexadecanoic acid as shown below.

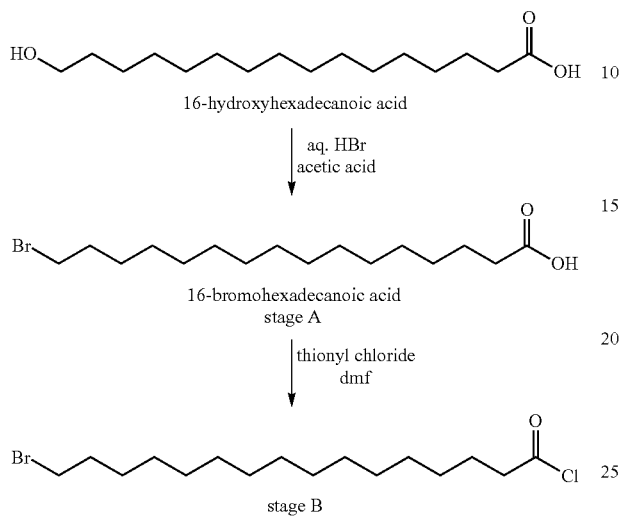

The novel compounds according to present invention i.e. 16-hydroxypalmitate of Paliperidone, 16-fluoropalmitate of Paliperidone and 16-bromopalmitate of Paliperidone were evaluated for physical appearance, color, odor, melting Point, boiling point, purity, NMR spectra and found to comply with the specifications.

The novel compounds according to present invention i.e. 16-hydroxypalmitate of Paliperidone, 16-fluoropalmitate of Paliperidone and 16-bromopalmitate of Paliperidone were characterized by $^1$H NMR. Spectrum as depicted in FIG. 1 and FIG. 2.

The pharmaceutical composition comprising 16-hydroxypalmitate of Paliperidone or 16-fluoropalmitate of Paliperidone or 16-bromopalmitate of Paliperidone along with one or more pharmaceutically acceptable excipient.

The pharmaceutical composition according to present invention contains suitable amount of 16-hydroxypalmitate of Paliperidone or 16-fluoropalmitate of Paliperidone or 16-bromopalmitate of Paliperidone as active ingredients. The pharmaceutical composition contains in the range of 0.05 mg to 1000 mg, preferably 0.5 mg to 800 mg of active ingredient.

The pharmaceutical composition according to present invention may be in the form of tablet, capsule, pill, solution, liquids, suspension, emulsion, syrup, ointment, cream, gel, lotions, pastes, spray, injection, inhalers, powder, sachet, granules, beads, suppositories, pessaries, liniments, elixirs, transdermal patches, foam, stick or drops.

The one or more pharmaceutically acceptable excipient present in the composition according to present invention may be selected from the group consisting of diluents, disintegrant, binders, lubricant, release modifier, plasticizers, solubilizing agent or emulsifying agent, surfactant, stabilizing agent, acidic agent, basic agent, sweeteners, flavour, pH regulating agent, osmotic or tonicity adjusting agents, chelating agents, buffers, bases, antioxidants/sequestrant, preservatives, solvents/co-solvents, thickeners/suspending agents, flocculating agents, complexing agents, colorants, gelling agents, humectant, adsorbents, permeation enhancer, opacifying agent and vehicles.

In another aspect of the present invention is to provide pharmaceutical composition comprising novel 16-hydroxypalmitate or 16-fluoropalmitate or 16-bromopalmitate of Paliperidone for the treatment of schizophrenia and schizoaffective disorder.

EXAMPLES

In the following example, the preferred embodiments of the present invention are described only by way of illustrating the process of the invention. However, these are not intended to limit the scope of the present invention in any way.

Example 1

Preparation of 16-hydroxypalmitate of Paliperidone
(3-(2-(4-(6-fluorobenzo[d]isoxazol-3-yl)piperidin-1-yl)ethyl)-2-methyl-4-oxo-6,7,8,9-tetrahydro-4H-pyrido[1,2-a]pyrimidine-9-yl 16-hydroxyhexadecanoate)

Step I:
A mixture of Paliperidone (0.6983 gm), Potassium Carbonate (0.497 gm), Dichloromethane (20 mL) and 4-dimethylaminopyridine (0.07 gm) was stirred at room temperature (30° C.) for 30 minutes.

Step II:
Prepared the solution mixture of 16-hydroxyhexadecanoyl chloride (1.0 gm) and Dichloromethane (25 mL).

Step III:
Started dropwise addition of solution from step II slowly in 4 lot at room temperature (30° C.) to the mixture of step I and each lot addition in 15-20 minutes. Each lot addition stirred for 10 minutes at room temperature (30° C.). After addition reaction mixture stirred at room temperature (30° C.) for 16-18 hours. Checked the reaction mixture by TLC.

Step IV:
After completion of reaction, the reaction mixture was filtered through Hyflow bed. Washed Hyflow bed with Dichloromethane (20 mL). The clear filterate was washed with 10% sodium carbonate (30 mL×2). The organic layer was concentrated via rota vapour under vaccum at 40-50° C., then stripped out with acetone (5 mL×2) to obtained mass. Added ethanol (20 mL) and heated it to get clear solution. Then cooled to room temperature naturally and filtered it and to this obtained solid 10 mL of ethanol was added and heated it to get clear solution. Finally cooled to room temperature naturally and filtered the final product i.e. 16-hydroxypalmitate of Paliperidone which is characterised by $^1$H NMR Spectrum as depicted in FIG. 2. $^1$H NMR (CDCl$_3$, 500 MHz, δ ppm): 1.30 (m, 22H), 1.41 (m, 2H), 1.65 (m, 2H), 1.76 (m, 2H), 2.01 (m, 1H), 2.10 (m, 6H), 2.28 (m, 2H), 2.32 (s, 3H), 2.39 (m, 2H), 2.54 (t, 2H), 2.78 (m, 2H), 3.08 (m, 2H), 3.17 (m, 2H), 3.54 (t, 2H), 4.01 (dd, 1H), 5.77 (t, 1H), 7.05 (td, 1H), 7.24 (dd, 1H), 1.71 (q, 1H).

Example 2

Preparation of 16-fluoropalmitate of Paliperidone
(3-(2-(4-(6-fluorobenzo[d]isoxazol-3-yl)piperidin-1-yl)ethyl)-2-methyl-4-oxo-6,7,8,9-tetrahydro-4H-pyrido[1,2-a]pyrimidine-9-yl 16-fluorohexadecanoate)

Step I:
A mixture of Paliperidone (0.0680 gm), Potassium Carbonate (0.0484 gm), Dichloromethane (5 mL) and 4-dimethylaminopyridine (0.007 gm) was stirred at room temperature (30° C.) for 30 minutes.

Step II:

Prepared the solution mixture of 16-fluorohexadecanoyl chloride (0.100 gm) and Dichloromethane (10 mL).

Step III:

Started dropwise addition of solution from step II slowly in 4 lot at room temperature (30° C.) to the mixture of Step I and each lot addition in 15-20 minutes. Each lot addition stirred for 10 minutes at room temperature (30° C.). After addition reaction mixture stirred at room temperature (30° C.) for 16-18 hours. Checked the reaction mixture by TLC.

Step IV:

After completion of reaction, the reaction mixture was filtered through Hyflow bed. Washed Hyflow bed with Dichloromethane (20 mL). The clear filterate was washed with 10% sodium carbonate (6 mL×2). The organic layer was separated and added pinch of sodium sulphate to remove moisture and then concentrated. Concentrated mass was taken for column chromatography. Then a mixture of dichloromethane and Methanol in the ratio of (98:2) was used as solvent to remove the product fraction. Non-polar elute, product elute was collected separately. Each fraction was concentrated and evaluated by TLC and finally obtained oily mass of 16-fluoropalmitic of Paliperidone which is characterised by $^1$H NMR Spectrum as depicted in FIG. 1. $^1$H NMR (CDCl$_3$, 500 MHz, δ ppm): 1.30 (m, 22H), 1.41 (m, 2H), 1.65 (m, 2H), 1.76 (m, 2H), 2.01 (m, 1H), 2.10 (m, 6H), 2.28 (m, 2H), 2.32 (s, 3H), 2.39 (m, 2H), 2.54 (t, 2H), 2.78 (m, 2H), 3.08 (m, 2H), 3.17 (m, 2H), 3.54 (t, 2H), 4.01 (dd, 1H), 7.05 (td, 1H), 7.24 (dd, 1H), 1.71 (q, 1H).

Example 3

Preparation of 16-bromopalmitate of Paliperidone (3-(2-(4-(6-fluorobenzo[d]isoxazol-3-yl)piperidin-1-yl)ethyl)-2-methyl-4-oxo-6,7,8,9-tetrahydro-4H-pyrido[1,2-a]pyrimidine-9-yl 16-bromohexadecanoate)

Step I:

A mixture of Paliperidone (0.5586 gm), Potassium Carbonate (0.397 gm), Dichloromethane (20 mL) and 4-dimethylaminopyridine (0.06 gm) was stirred at room temperature (30° C.) for 30 minutes.

Step II:

Prepared the solution mixture of 16-bromohexadecanoyl chloride (1.0 gm) and Dichloromethane (25 mL).

Step III:

Started dropwise addition of solution from step II slowly in 4 lot at room temperature to the mixture of step I and each lot addition in 15-20 minutes. Each lot addition stirred for 10 minutes at room temperature (30° C.). After addition the reaction mixture stirred at room temperature (30° C.) for 16-18 hours. Checked the reaction mixture by TLC.

Step IV:

After completion of reaction, the reaction mixture was filtered through Hyflow bed. Washed Hyflow bed with Dichloromethane (20 mL). The clear filterate was washed with 10% sodium carbonate (20 mL×2). The organic layer was concentrated via rota vapour under vaccum at 40-50° C. Concentrated mass was taken for column chromatography. Then a mixture of dichloromethane and Methanol in the ratio of (98:2) was used as solvent to remove the product fraction. Non-polar elute, product elute was collected separately. Each fraction was concentrated and checked by TLC and finally obtained oily mass of 16-bromopalmitic of Paliperidone.

The invention claimed is:

1. The compound of formula (II):

Formula (II)

Wherein, R = C$_{10}$-C$_{21}$ alkyl substituted by hydroxy or halogen

2. The compound according to claim 1 having formula:

Wherein, R=C$_{16}$ alkyl substituted by hydroxy.

3. The compound according to claim 1 having formula:

Wherein, R=C$_{16}$ alkyl substituted by halogen.

4. The compound according to claim 3 wherein halogen substitution in R is selected from the group consisting of F, Cl, Br and I.

5. The compound according to claim 4, wherein halogen substitution in R is F or Br.

6. A pharmaceutical composition comprising i) a compound according to claim 1; and ii) one or more pharmaceutically acceptable excipients.

7. A process of preparing compound of formula (II), wherein the process comprises the step of reacting Paliperidone with one or more intermediates; optionally along with one or more solvents and/or reagents

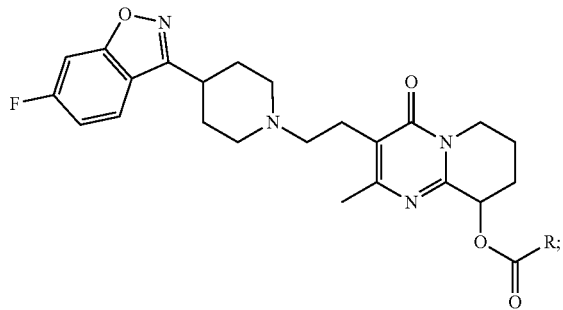

Formula (II)

Wherein R = $C_{10}$-$C_{21}$ alky substituted by hydroxy or halogen.

8. The process according to claim 7, wherein one or more intermediates is selected from compound of formula,

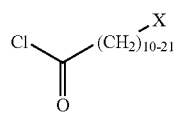

Wherein X=hydroxy or halogen,
hydroxy or halogen substituted anhydride, hydroxy or halogen substituted mixed anhydride.

9. The process according to claim 8, wherein one or more intermediates is selected from 16-hydroxyhexadecanoyl chloride, 16-fluorohexadecanoyl chloride or 16-bromohexadecanoyl chloride.

10. The process according to claim 7, wherein one or more solvents is selected from dichloromethane, methanol, acetone, ethanol, methyl ethyl ketone, methyl isobutyl ketone, dibutyl ketone, diethyl ketone, dipropyl ketone, diisopropyl ketone, methyl butyl ketone, methyl propyl ketone, methyl isopropyl ketone, ethyl isopropyl ketone, propanol, isopropanol, butanol, isobutanol, t-butanol, pentanol, dichloroethane, chloroform, carbon tetrachloride, tetrahydrofuran, dioxane, diethyl ether, diisopropyl ether, dibutyl ether, methyl tertiary butyl ether, methyl ethyl ether, methyl isobutyl ether, ethyl acetate, propyl acetate, isopropyl acetate, butyl acetate, tertiary butyl acetate, pentyl acetate, acetonitrile, propionitrile or mixtures thereof.

11. The process according to claim 7, wherein one or more reagents is selected from potassium carbonate, 4-dimethylaminopyridine, sodium carbonate, sodium sulphate, potassium sulphate, potassium carbonate, sodium hydroxide, potassium hydroxide, sodium bicarbonate, potassium bicarbonate, lithium hydroxide, lithium carbonate, triethylamine, diisopropylamine, pyridine or mixtures thereof.

\* \* \* \* \*

UNITED STATES PATENT AND TRADEMARK OFFICE
CERTIFICATE OF CORRECTION

PATENT NO. : 11,377,445 B2
APPLICATION NO. : 16/962718
DATED : July 5, 2022
INVENTOR(S) : Sivakumar Venkata Bobba et al.

It is certified that error appears in the above-identified patent and that said Letters Patent is hereby corrected as shown below:

On the Title Page

Item (54) and in the Specification, Column 1, Lines 1-3, Add "NOVEL" as the first word of the title.

Signed and Sealed this
Fourth Day of October, 2022

Katherine Kelly Vidal
*Director of the United States Patent and Trademark Office*